US00RE34281E

United States Patent [19]

Gracey

[11] E Patent Number: Re. 34,281

[45] Reissued Date of Patent: Jun. 15, 1993

[54] REMOVAL OF IODINE OR IODIDE IMPURITIES

[75] Inventor: Benjamin P. Gracey, Hull, England

[73] Assignee: BP Chemicals Limited, London, England

[21] Appl. No.: 831,889

[22] Filed: Feb. 6, 1992

Related U.S. Patent Documents

Reissue of:

[64] Patent No.: 4,975,155
Issued: Dec. 4, 1990
Appl. No.: 409,126
Filed: Sep. 19, 1989

[30] Foreign Application Priority Data

Sep. 27, 1988 [GB] United Kingdom ..... 8822661

[51] Int. Cl.[5] ..... B01D 3/34

[52] U.S. Cl. ..... 203/38; 203/DIG. 6; 560/248; 562/608

[58] Field of Search ..... 203/38, DIG. 6, DIG. 21, 203/91; 562/608; 560/248

[56] References Cited

U.S. PATENT DOCUMENTS 3,658,467 4/1972 Maeck ..... 55/75
3,772,156 11/1973 Johnson et al. ..... 203/33
4,615,806 10/1986 Hilton ..... 210/690
4,664,753 5/1987 Erpenbach et al. ..... 203/38

FOREIGN PATENT DOCUMENTS 0196173 10/1986 European Pat. Off. .
0217191 6/1988 European Pat. Off. .
0296584 12/1988 European Pat. Off. .
3329781 2/1985 Fed. Rep. of Germany .

*Primary Examiner*—Virginia Manoharan
*Attorney, Agent, or Firm*—Brooks Haidt Haffner & Delahunty

[57] ABSTRACT

A process for removing iodine or soluble iodide impurities from a carboxylic acid or carboxylic acid anhydride, the carboxylic acid or carboxylic acid anhydride having been by a carbonylation process. The process includes: step (a) treating impure carboxylic acid or carboxylic acid anhydride containing iodine or soluble iodide impurities with an unsupported scavenger at a temperature of between 20° and 250° C. and step (b) thereafter separating the treated carboxylic acid or carboxylic acid anhydride from the scavenger. The scavenger is a silver salt in the absence of a trialkyl phosphine, a triaryl phosphine and a heterocyclic aromatic nitrogen compound. The preferred scavenger for acetic acid and acetic anhydride is silver acetate.

7 Claims, No Drawings

REMOVAL OF IODINE OR IODIDE IMPURITIES

Matter enclosed in heavy brackets [ ] appears in the original patent but forms no part of this reissue specification; matter printed in italics indicates the additions made by reissue.

The present invention relates to a process for removing iodine or iodide impurities from the products of carbonylation processes. In particular the present invention relates to the removal of iodine or iodide impurities from carboxylic acid or carboxylic acid anhydrides prepared by the rhodium catalysed carbonylation of alcohols, olefins or esters.

The uss of rhodium/iodide catalysts to effect the carbonylation of alcohols (eg methanol to acetic acid), olefins (eg ethylene to propionic acid) and esters (e.g. methyl acetate to acetic anhydride) is well known. It is also known that the carboxylic acid or carboxylic acid anhydride products tend to retain iodide, in the forms of iodine or soluble iodides, which must be subsequently removed.

A number of methods have been developed to effect iodide removal and some are operated commercially on plant using carbonylation technology. U.S. Pat. No. 4,029,553 describes a distillation process for generating high purity acetic acid containing less than 20 parts per billion iodide. A different approach is described in U.S. Pat. No. 3,772,156 which discloses a two column distillation process in which the crude acetic acid is contacted with an alkali or alkaline earth metal compound either alone or in combination with hypophosphorus acid. Finally U.S. Pat. No. 3,709,795 discloses a process for removing halide impurities from acetic acid which involves the use of a strong inorganic oxidising agent such as potassium permanganate. Whilst effective, this latter process is not easy to carry out commercially.

Other approaches of interest include the use of a silver ionexchange resin (EP No. 196173) and the use of a peracid (DE No. 3612504)

U.S. Pat. No. 4,664,753 discloses a particularly effective method of removing iodine and soluble iodide impurities from the products of carbonylation processes. This patent describes contacting the product with a mixture of (a) an alkyl or aryl phosphine or a heterocyclic aromatic nitrogen compound and (b) a metal selected from copper, silver, zinc or cadmium.

A problem arises with the approach described in U.S. Pat. No. 4,664,753 in that when such a two component system is employed there is a possibility of contaminating the carbonylation product with the first of the above mentioned components. Hence the problem to be solved is the prevention of such contamination whilst maintaining an efficient scavenging system.

Accordingly, the present invention provides a process for removing iodine or soluble iodide impurities from a carboxylic acid or carboxylic acid anhydride, the carboxylic acid or carboxylic acid anhydride having been produced by a carbonylation process, which process comprises step (a) treating impure carboxylic acid or carboxylic acid anhydride containing iodine or soluble iodide impurities with an unsupported scavenger at a temperature of between 20° and 250° C. and step (b) thereafter separating the treated carboxylic acid or carboxylic acid anhydride from the scavenger characterised in that the scavenger consists of a silver salt in the absence of a trialkyl phosphine, a triaryl phosphine and a heterocyclic aromatic nitrogen compound.

The invention solves the problem by selecting from U.S. Pat. No. 4,664,753 a metal (silver) which is more effective without a phosphine or heterocyclic aromatic nitrogen compound. This is unexpected because U.S. Pat. No. 4,664,753 suggests (see Examples 1 and 3) that a phosphine is needed in order to obtain a product of high purity.

The silver salt can be any one which will react with iodide to generate insoluble silver iodide. Preferably, the salt should be soluble in the carboxylic acid or carboxylic acid anhydride. It is most preferred, if possible to use a silver salt having an anion corresponding to the carboxylic acid being treated. Thus for acetic acid, silver acetate is most preferred whilst for propionic acid silver propionate should be used.

It is also possible to use suspensions of silver salts if the silver salt is insoluble or sparingly soluble in the liquid medium being purified. In these cases, it is preferred that the suspension is finely divided.

The process of the present invention, is particularly suitable for treating carboxylic acids or carboxylic acid anhydrides having up to 300 ppm iodine or soluble iodide impurities. The silver is recovered from the process as silver iodide which can either be disposed of or treated to regenerate the appropriate silver salt. The scavenger and the carboxylic acid or carboxylic acid anhydride are kept in contact until substantially all the iodine or iodide is scavenged. For a process operating under a preferred temperature in the range 80° to 150° C., a suitable contact time is one in the range 10 to 100 minutes. The mixture may be stirred or otherwise agitated if desired. Typically the process of the present invention is able to reduce the level of iodine or soluble iodide impurities to levels in the order of less than 100 parts per billion, preferably to less than 20 parts par billion.

The process of the present invention is particularly suitable for use in purifying (a) acetic acid produced by rhodium/iodide catalysed methanol carbonylation, (b) propionic acid produced by rhodium/iodide catalysed ethylene carbonylation and (c) acetic anhydride produced by rhodium/iodide catalysed carbonylation of methyl acetate. However, the process is equally applicable to kettles for processes using carboxylic acids and carboxylic acid anhydride feedstocks in conjunction with iodide sensitive catalysts (e.g. vinyl acetate monomer production).

The invention will now be illustrated by reference to the following Examples.

BATCH REACTIONS—GENERAL METHOD

A 500 ml three necked round bottomed flask was equipped with a Eurotherm controlled heating mantle, a thermo-couple pocket, two wide bore taps—one connected to a Liebig condenser and the other to a stillhead condenser and receiver. The flask was charged with 450 ml of the impure acetic acid (iodide level as determined by neutron activation analysis), the prerequisite amount of scavenger and a few antibumping granules. Both the condenser and the distillation apparatus were purged with nitrogen.

With the tap open to the condenser only, the apparatus was brought to a gentle reflux (simmer). After 1 hour the second tap was opened and the first closed. The reflux was increased to rapid distillation of the treated acetic acid. The experiment was terminated when 90% of the acetic acid had been collected. The distilled acetic acid was analysed for total iodide content (by neutron activation analysis).

EXAMPLES 1 AND A TO C

Compare a silver acetate salt with copper (II) acetate and two scavenger systems according to U.S. Pat. No. 4,664,753. Examples A to C do not constitute part of the invention. The results (Table 1) show the unexpected superiority of silver acetate in the absence of a phosphine.

TABLE 1

| Example | Scavenger | % w/w Scavenger | Initial Iodide (ppb) | Final Iodide (ppb) | % Removal |
|---|---|---|---|---|---|
| 1 | Silver Acetate | 0.03 | 991 | 50 ± 2 | 95 |
| A | Silver Acetate + Triphenyl-phosphine | 0.03 of each | 662 | 653 ± 40 | 0 |
| B | Copper (II) Acetate | 0.03 | 991 | 850 ± 100 | 0 |
| C | Copper (II) Acetate + Triphenyl-phosphine | 0.03 of each | 1380 | 800 ± 47 | 42 |

We claim:

1. A process for removing iodine or soluble iodide impurities from a carboxylic acid or carboxylic acid anhydride, the carboxylic acid or carboxylic acid anhydride having been produced by a carbonylation process, which process consists essentially of (a) treating the carboxylic acid or carboxylic acid anhydride containing iodine or soluble iodide impurities with a soluble silver salt in the absence of a trialkyl phosphine, a triaryl phosphine and a heterocyclic nitrogen compound, and step (b) thereafter separating the treated carboxylic acid and carboxylic acid anhydride by distillation from silver iodide produced in step (a), wherein the impure carboxylic acid or carboxylic acid anhydride contains [at least] *up to* 300 parts per million by weight in total of iodine and soluble iodide impurities and the treated carboxylic acid or carboxylic acid anhydride contains less than 100 parts per billion by weight in total of iodine and soluble iodide impurities.

2. The process as claimed in claim 1 wherein the silver salt is silver acetate.

3. The process as claimed in claim 1 wherein the silver salt is the silver salt of the carboxylic acid or carboxylic acid anhydride which is treated.

4. The process as claimed in claim 1 wherein the carboxylic acid or carboxylic acid anhydride is chosen from the group consisting of acetic acid, propionic acid and acetic anhydride.

5. The process as claimed in claim 1 wherein the step (a) is carried out at a temperature in the range 80°–150° C.

6. The process as claimed in claim 1 wherein the carboxylic acid or carboxylic acid anhydride is treated with the silver salt for a period of time in the range from 10 to 100 minutes.

7. The process as claimed in claim 1 wherein the treated carboxylic acid or carboxylic acid anhydride contains less than 20 parts per billion by weight in total of iodine and soluble iodide impurities.

* * * * *